United States Patent [19]

Rogers et al.

[11] Patent Number: 4,635,471

[45] Date of Patent: Jan. 13, 1987

[54] HARDNESS TESTING DEVICE FOR PIPES

[75] Inventors: D. Brett Rogers, Poland; Kevin T. Penner, Salem, both of Ohio

[73] Assignee: Energy Development Corporation, East Liverpool, Ohio

[21] Appl. No.: 819,415

[22] Filed: Jan. 16, 1986

[51] Int. Cl.[4] .............................................. G01N 3/42
[52] U.S. Cl. .......................................... 73/81; 73/78; 409/133
[58] Field of Search .................. 73/81, 78, 83; 408/2; 409/133

[56] References Cited

U.S. PATENT DOCUMENTS

| | | | |
|---|---|---|---|
| 2,126,175 | 8/1938 | Dalcher | 73/78 |
| 2,252,993 | 8/1941 | Stewart | 409/133 X |
| 2,259,840 | 10/1941 | Smith | 73/78 |
| 2,690,702 | 10/1954 | Romans et al. | 409/133 X |
| 2,839,917 | 6/1958 | Webster | 73/81 |
| 3,123,997 | 3/1964 | Cosner | 73/81 |
| 3,236,124 | 2/1966 | Rhoades | 408/2 |
| 3,295,363 | 1/1967 | Delporte | 73/81 |
| 3,802,316 | 4/1974 | Bohm et al. | 409/133 X |
| 4,061,020 | 12/1977 | Fridley et al. | 73/83 X |
| 4,435,975 | 3/1984 | Edward, Jr. | 73/78 X |

Primary Examiner—Howard A. Birmiel
Assistant Examiner—Tom Noland
Attorney, Agent, or Firm—Harpman & Harpman

[57] ABSTRACT

A hardness tester for pipes comprising a positioning mechanism that presents the pipe to a multiple purpose testing head having a pre-programmed proportional control configuration that independently engages the pipe and determines the pipes relative position to that of the program controlled testing head which contains independent pre-programmed testing heads. The pipe is prepared for testing by cleaning a small test portion of the pipe, engagement of a load cell assembly to the clean pipe portion determining material hardness.

8 Claims, 9 Drawing Figures

HARDNESS TESTING DEVICE FOR PIPES

BACKGROUND OF THE INVENTION

1. Technical Field

Devices of this type have used a variety of different and separate testing procedures to clean a small portion of the material to be tested and then determine the hardness of the material which is critically important in determining use characteristics and requirements.

2. Description of the Prior Art

Prior art devices of this type have relied on a variety of different holding and testing configurations. See for example U.S. Pat. Nos. 3,020,752, 2,126,175 and 2,690,702.

In U.S. Pat. No. 3,020,752, a device is disclosed that uses electromagnets to stabilize and hold the test piece in position for a movable hardness tester.

U.S. Pat. No. 2,126,175 discloses a testing machine that determines hardness of material by speed and pressure required on a drill that engages the material.

In U.S. Pat. No. 2,690,702, a combined testing device for use on materials is shown.

SUMMARY OF THE INVENTION

A hardness tester for pipes that provides an automatic positioning and holding of a work piece for testing and a pre-programmed, self-correcting prositioning of a multi-equipped testing head. The testing head combines both a cleaning and hardness testing function in a single configuration that has a pre-programmed controlled position by synchronized multiple servodrive motors in a position feed back configuration. A variety of pipes sizes and materials can be tested continuously in an automatic manner.

DESCRIPTION OF THE PREFERRED EMBODIMENT

Figure 1:
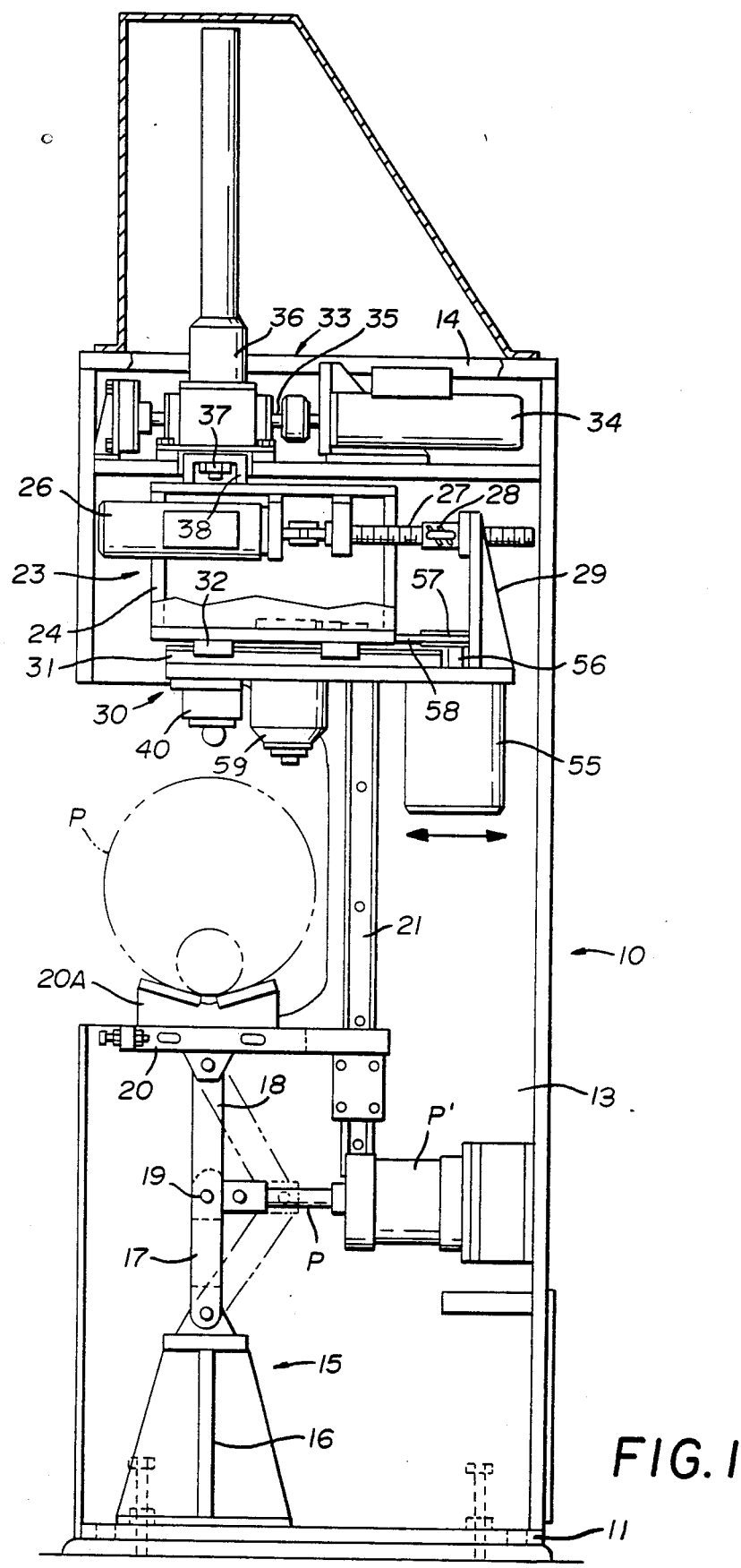
FIG. 1 is a side elevation of a hardness testing device.
Figure 2:
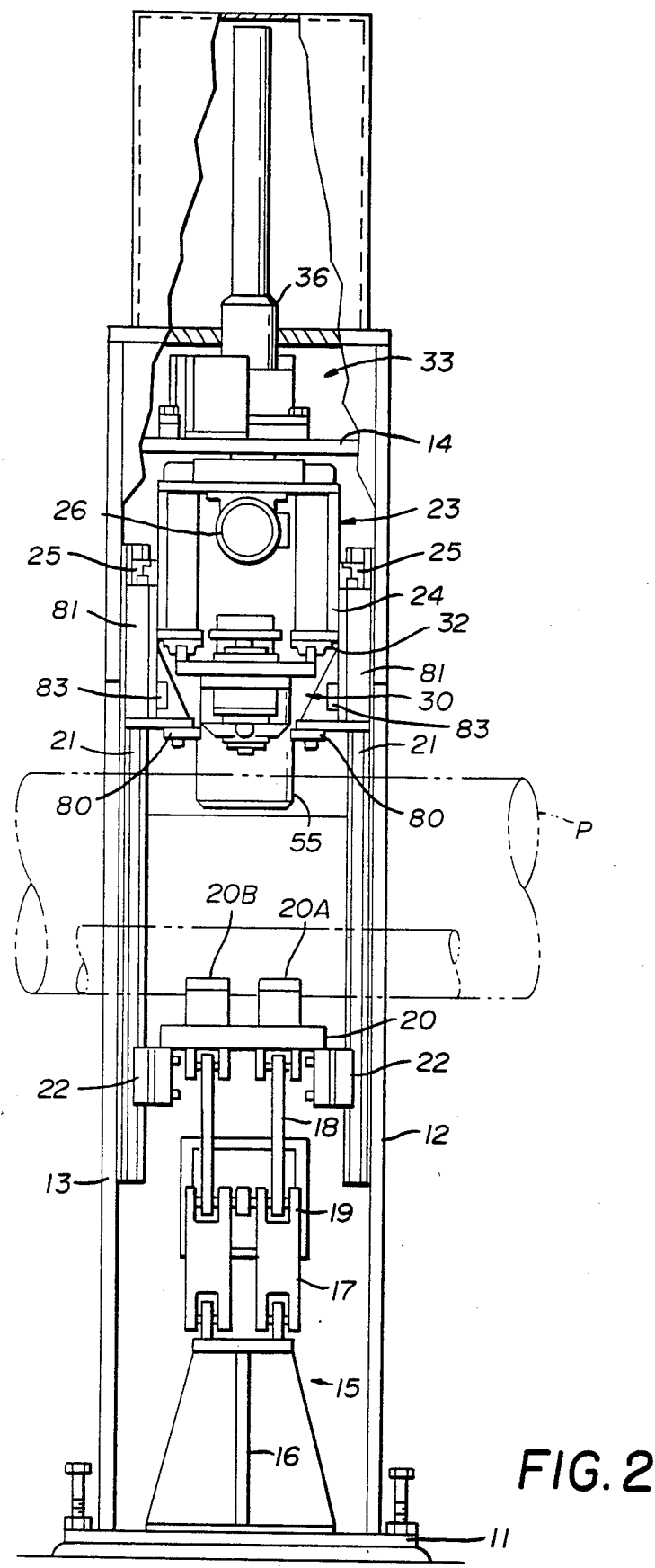
FIG. 2 is a front elevation of the hardness testing device.

A hardness tester can be seen in FIGS. 1 and 2 of the drawings comprising a generally C-shaped frame configuration 10 having a base 11, vertical frame members 12 and 13 with right angularly extending head support framework 14 in oppositely disposed relation to said base 10. A work piece support and positioning stand 15 has a structural I-shaped member 16 from which multiple support links 17 and 18 extend. The links are pivoted to one another at 19 with links 17 being pivotally secured at one end to and extending from the stand 15. The free ends of the links 18 are pivoted to a work piece fixture 20 having a pair of upstanding support brackets 20A and 20B, the upper surfaces of which are tapered longitudinally from their oppositely disposed outer ends. A piston rod P of a piston and cylinder assembly P' is secured to the pivot 19 for reciprocation of the links as indicated by the broken lines in FIG. 1 of the drawings. The fixture 20 is movably positioned in a pair of spaced vertically aligned guide tracks 21 via guides 22 secured thereto. A testing and milling head assembly 23 is positioned within the head support framework 14 and is generally characterized by its ability to move on both a vertical and horizontal plane separately or simultaneously. The head assembly 23 has a stabilizer frame 24 with a pair of vertical guide shoes 25 positioned on either side thereof as best seen in FIG. 2 of the drawings. The guide shoes 25 are registrable within said vertically aligned guide tracks 21 as hereinbefore described.

A horizontal drive motor 26 is secured to the stabilizer frame 24 and has a threaded screw drive shaft 27 extending outwardly therefrom. A screw follower 28 is positioned on the shaft 27 and has a vertically disposed frame member 29 extending downwardly therefrom and secured to a movable testing head support assembly 30. A pair of horizontally positioned guide tracks 31 are longitudinally aligned on the testing head support assembly 30 and register with correspondingly positioned guide members 32 extending downwardly from the stabilizer frame 24.

A vertical drive motor assembly 33 is secured within the head support framework 14 above and secured to the stabilizer frame 24. The vertical drive motor assembly comprises a motor 34 having a drive shaft 35 engaging a vertical ball jack 36 as is well known in the art. The vertical ball jack 36 has an activation shaft 37 that is secured to a bracket 38 on the upper side of the stabilizer frame 24.

It will be evident from the above description that by activating the vertical drive motor 34 the shaft 37 will advance downwardly from the position indicated in FIG. 1 of the drawings moving the attached stabilizer frame 24 in the guide tracks 21 along with it.

Horizontal movement of the test head support assembly 30 is achieved by activating the horizontal motor 26 with the corresponding movement of the screw follower 28 and support assembly 30 on the guide tracks 31 as indicated by the arrows in FIG. 1 of the drawings.

Figure 9:
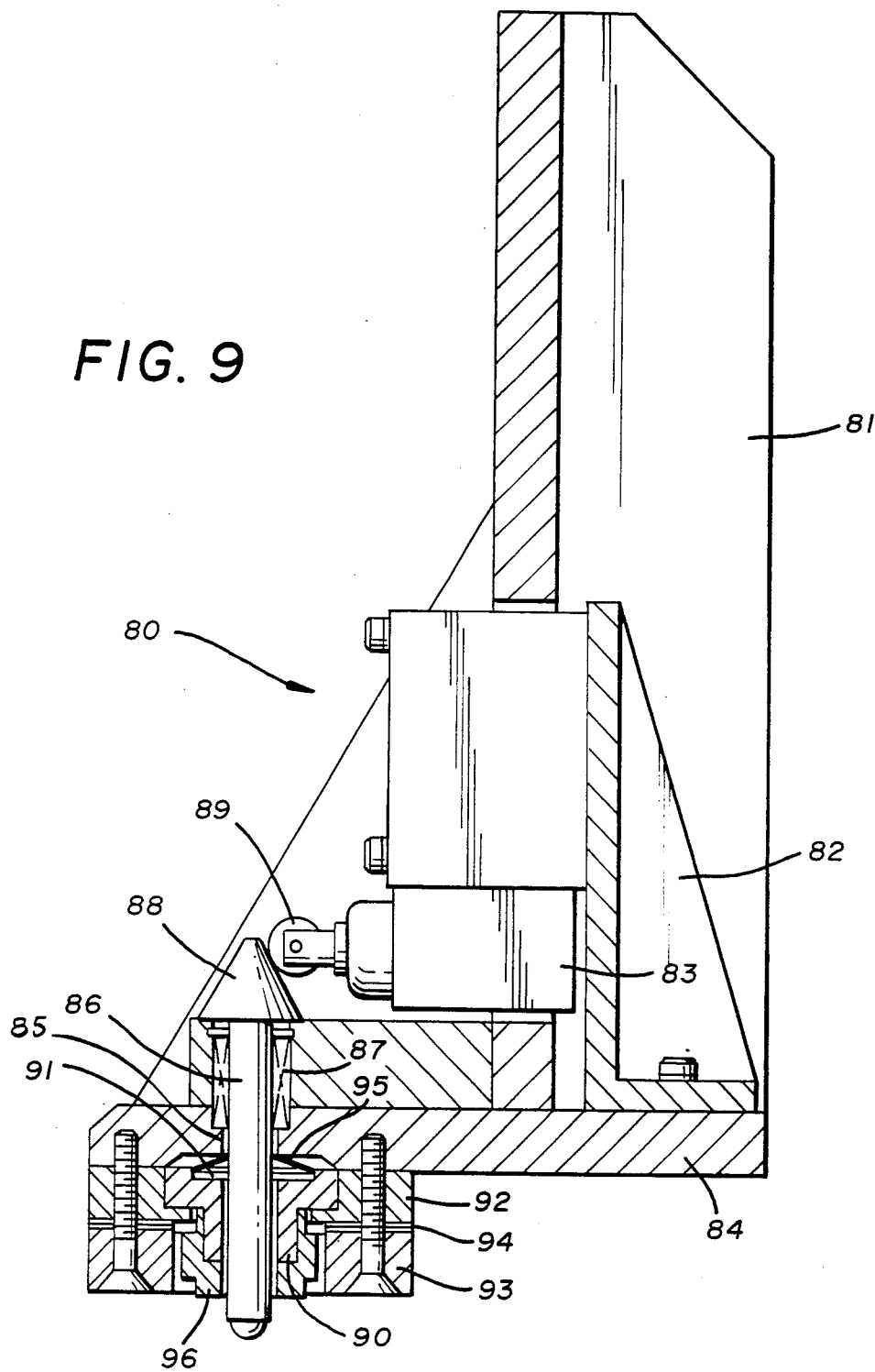
FIG. 9 is an enlarged cross sectional view of a clamping load cell assembly.

Referring now to FIGS. 2 and 9 of the drawings, a pair of clamping load cell assemblies 80 can be seen each having a main support arm 81 with an adjustable bracket 82. A limit switch 83 extends from the adjustable bracket 82. A load cell support bracket 84 is secured to the main support arm 81 and is apertured at 85 to receive a plunger 86 supported by bearings 87. The plunger 86 has a tapered top cap 88 that movably engages a limit switch follower 89. A clamping load cell 90 (manufactured by Houston Scientific International Inc., Model No. 1250) is positioned around the plunger 86 by a force washer 91 and held in place by a pair of retainer rings 92 and 93 separated by an adjustable shim 94. A spring washer 95 is positioned between the load cell 90 and support bracket 84 which allows for retraction of the clamping load cell 90 within the retainer rings 92 and 93.

Figure 6:
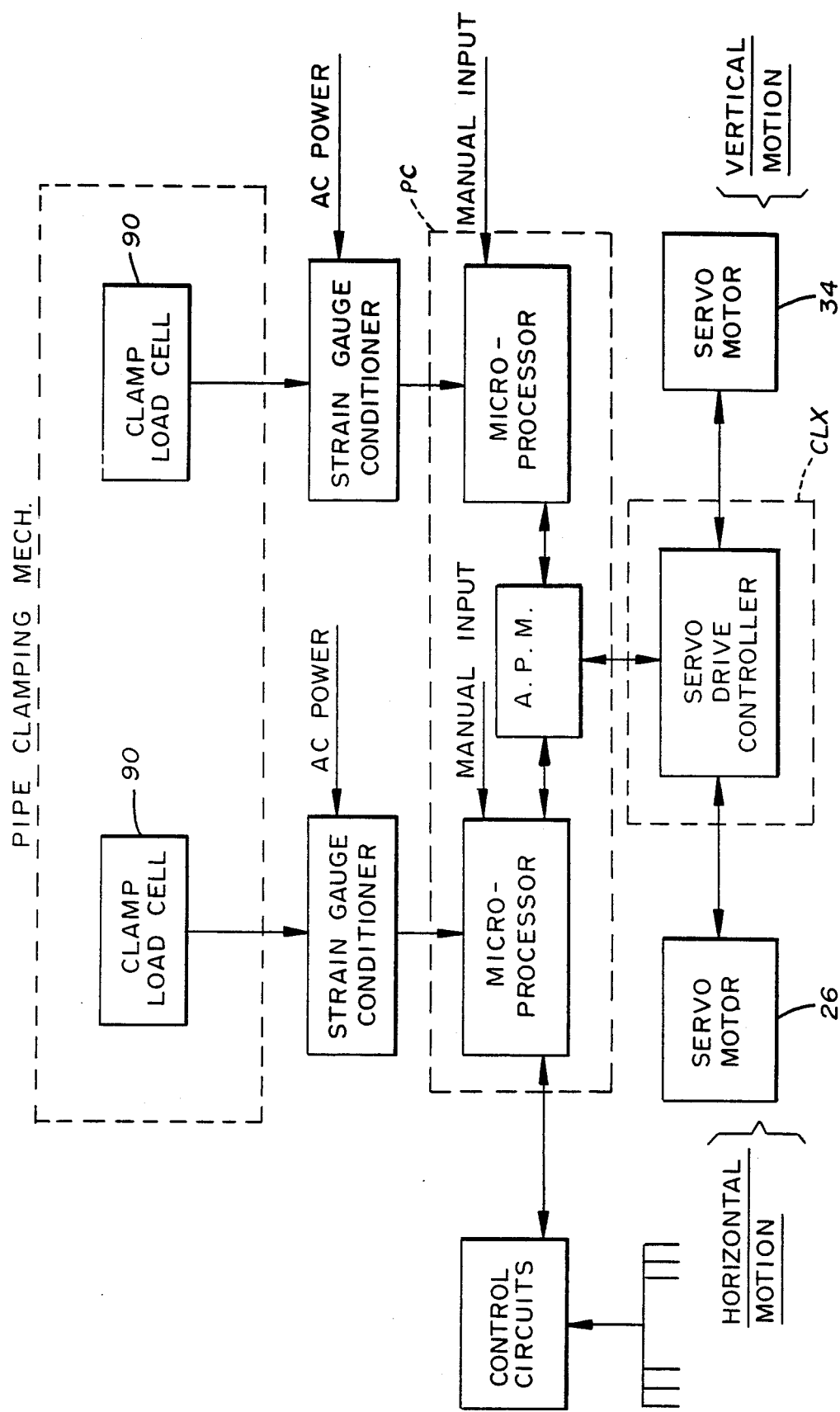
FIG. 6 is a block flow diagram of the pipe clamping electronic control mechanism.

In operation, the clamping load cell assemblies 80 determine initial test material registration and sense the proper clamping load prior to material preparation for testing. The clamping load cell assemblies 80 are interconnected in the test procedure as is shown in FIG. 6 of the drawings. Upon initial vertical displacement of the testing head support assembly 30, the plunger 86 engages the test material and moves upwardly activating the limit switch 83 starting a timing sequence in a controller (PC) (which will be described in greater detail later).

The timing sequence combined with the rate of displacement of the testing head support assembly 30 allows the controller (PC) to determine distance traveled upon initial contact by a nose piece 96 and compression of the clamping load cell 90 on which it is retained.

As the proper predetermined clamping load is achieved, the spring washer 95 is overcome allowing the clamping load cells 90 to retract within the retaining rings 93 and 92 as hereinbefore described.

Once the limit switch assemblies 83 and clamping load cells 90 have satisfied all pre-programmed parameters as determined by the controller (PC) the material preparation and testing sequence can begin as will be hereinafter described.

Figure 4:
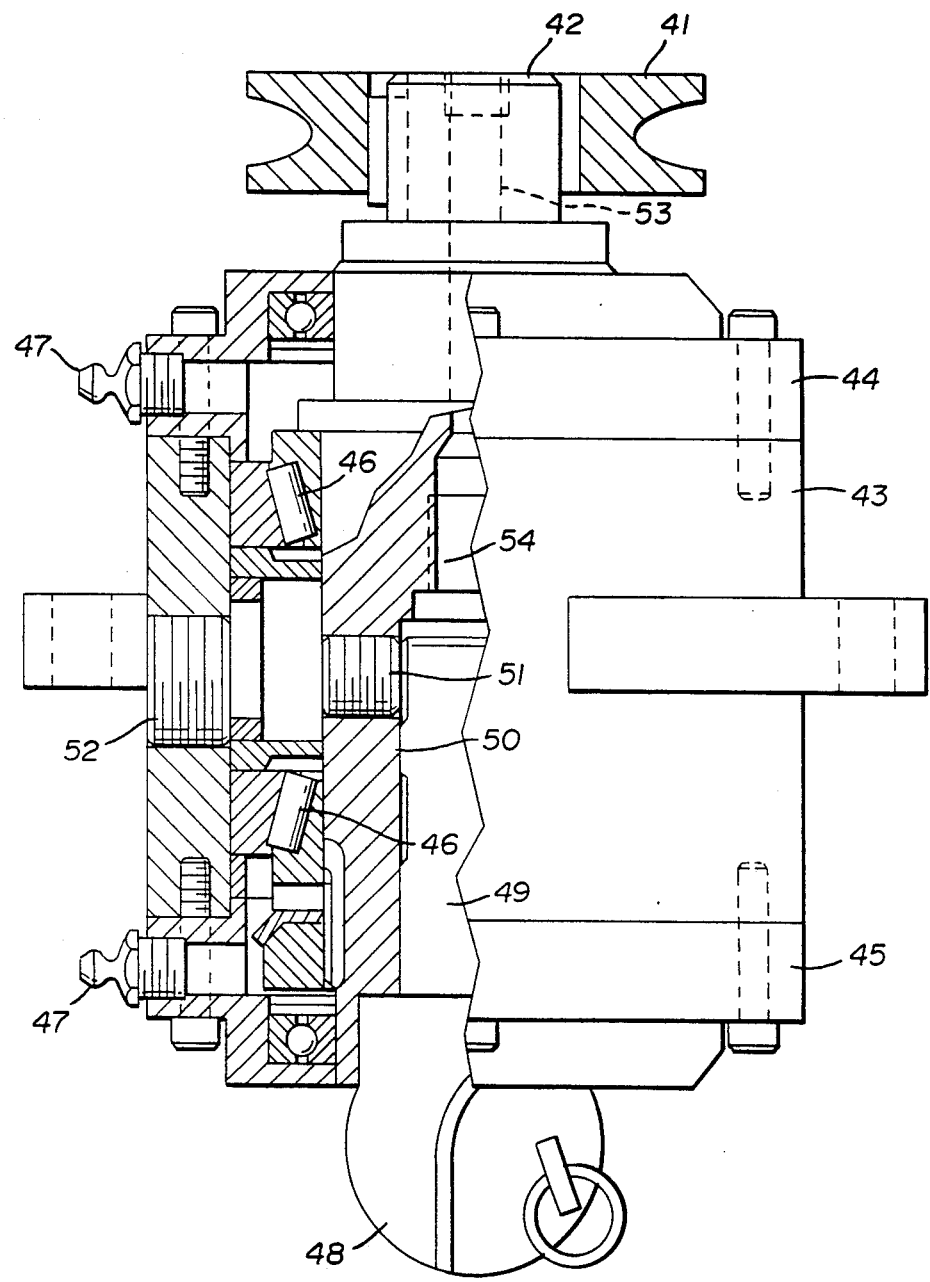
FIG. 4 is an enlarged partial cross section of a milling head.

A milling head assembly 40 is positioned within the head support assembly 30 and can best be seen in FIG. 4 of the drawings having a head drive pulley 41 and central drive spindle 42 rotatably positioned within a main body member 43 having apertured upper and lower closure plates 44 and 45. Bearing assemblies 46 and associated lubrication passages 47 are positioned in closure plates 44 and 45 as will be well understood by those skilled in the art.

A cutting tool 48 having a shank 49 is secured within a tool holder 50 defining the end of the spindle 42 and has a locking set screw 51 that secures the cutting tool 48 within the tool holder 50. An access plug 52 is aligned with said set screw in the main body member 43.

An axial bore 53 extending downwardly from the spindle top is threaded at its lower end 54. A mill head drive motor 55 is secured to the test head support assembly 30 having a drive shaft 56 and a pulley 57 on the end thereof. A drive belt 58 communicates between the pulley 57 and said head drive pulley 41 providing rotation to the same.

Figure 3:
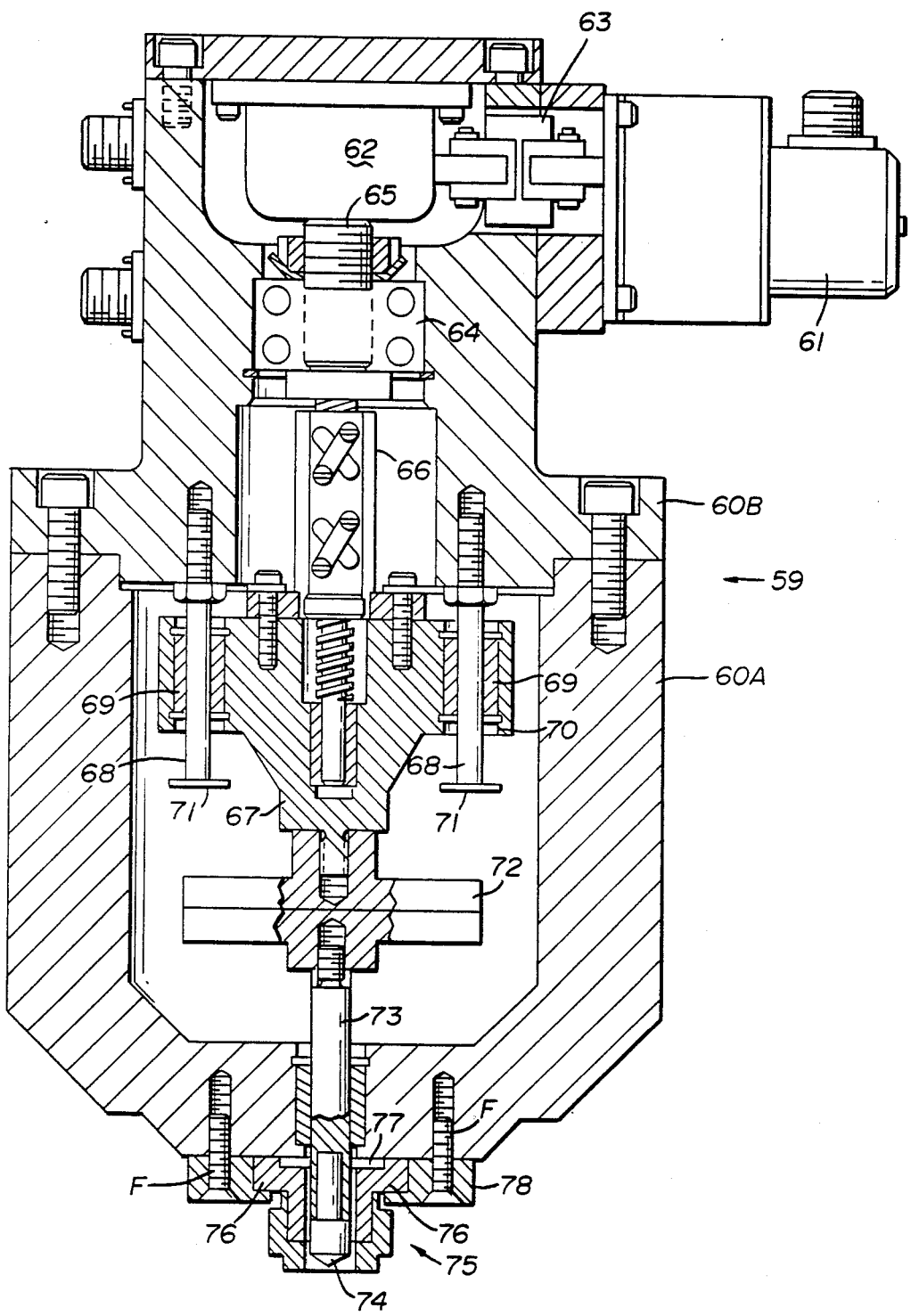
FIG. 3 is an enlarged cross sectional view of a testing head.

Referring now to FIG. 3 of the drawings, a hardness testing head assembly 59 can be seen comprising a two part housing 60A and 60B. A DC servodrive motor 61 is secured to the housing 60B and drives a gear box 62 within the housing via a coupling 63. A bearing assembly 64 supports an output shaft 65 which is axially aligned within the housings 60A and 60B. The shaft 65 is threaded and has a ball screw assembly 66 positioned thereon. A load cell stabilizer 67 is movably positioned within the housing 60A on stabilizer guide rods 68 that extend through slide bearings 69 in oppositely disposed bores 70 within the stabilizer 67. Each of the guide rods 68 have a disc-like stop 71 on its free end and is secured to the housing 60B at its opposite end. A testing load cell 72 is secured to the stabilizer 67 in axial alignment with the shaft 65 and has a plunger shaft 73 extending downwardly therefrom. The testing load cell 72 is well known in the art and in this example is manufactured by Houston Scientific International, Inc. Model 1350. The plunger shaft 73 extends in an opening in the housing 60A and has a diamond penetrator 74 secured to the end thereof. A clamping load cell assembly 75 is secured to the lower end of the housing 60A around the plunger shaft 73. The clamping load cell assembly comprising clamping load cell 76 manufactured by Houston Scientific International, Inc., Model 1250 held in positioned by a force washer 77 and a load cell retaining ring 78 secured to the housing by fasteners F.

Referring now to FIGS. 5, 6, 7 and 8 of the drawings, the control of the entire testing sequence which includes positioning and elevation of the test pipe (P), the vertical and horizontal movement of the testing and milling head assembly 23 is servo-controlled by a GE Series Six Programmable Controller (PC), Part No. 1C600CP241A and a GE Axis Positioning Module (APM) Type 1, part No. 1C600 BF915C via a Gould Inc. servodrive system (CLX).

The axis positioning module (APM) is an intelligent, fully programmable single axis positioning controller integrated into the PC system. The APM provides a real time interface between the PC and a servo-controlled axis. Due to the complete integration of the APM into the PC system, the PC provides a predictable yet flexible axis control capability. The APM is distinguished by its use of resolvers (R) to provide postion feedback and by the programming of velocity and acceleration in terms of rates.

Figure 7:
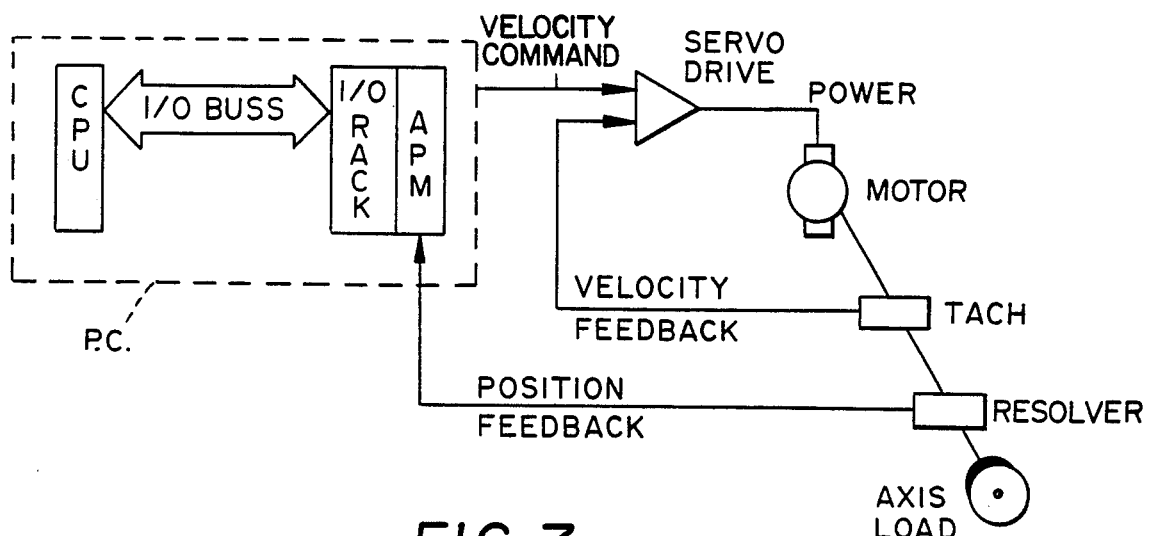
FIG. 7 is a block diagram of a control unit and motor driven system.
Figure 8:
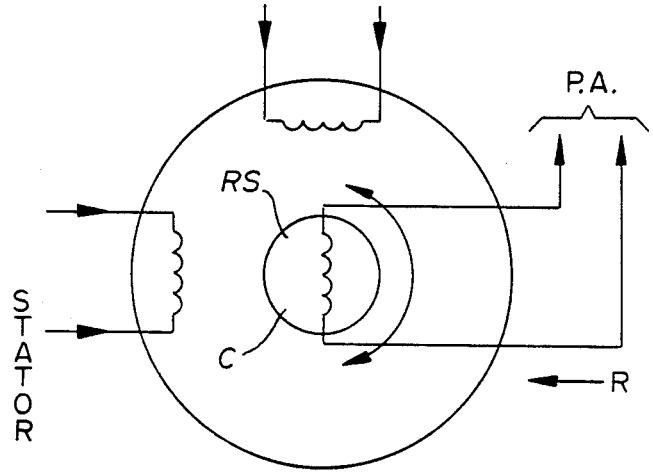
FIG. 8 is a graphic representation of a resolver.

The resolver (R) can be seen in FIGS. 7 and 8 of the drawings as a rotary transformer in which the phase relationship between its primary windings and secondary windings is controlled by the shaft position. Two primary coils, 90° mechanically and electrically out of phase, are located on a stator. A secondary coil (C) rotates with the rotor shaft (RS). The APM provides two excitation signals identical in amplitude but 90° out of phase to the two stator coils; the phase angle (PA) of the voltage induced in the secondary coil is directly proportional to the mechanical shaft angle as will be well understood by those skilled in the art.

The APM is positioned in a Series Six I/O rack where it is serviced by the Series Six Central Processing Unit (CPU) in the course of a normal CPU scan. The CPU communicates with the APM via a I/O bus using standard Series Six protocol. The APM translates the positioning commands received from the CPU into a position versus time profile, determines the current position of the axis using the input from a positioned feed back device, in this case a resolver, and compares it with the command position indicated by the profile. The profile is accomplished through software programming.

This process results in a velocity command output to a servo-drive which moves the axis or axes.

The CLX Servo Drive System consists of servo amplifier modules and power supply. Each amplifier module is capable of controlling one DC servo motor. Three motors that would be controlled by the CLX Servo Drive are the motor 34 of the vertical drive assembly, the motor 61 of the hardness testing device and motor 26 of the heat testing assembly 23.

All external signals are fed into the amplifier module, see FIG. 6 of the drawings, via a removable personality board. Compensation for specific motor parameters (tack voltage, velocity command, input sensitivity, etc.) as well as selection of internal amplifier options (accel-decel, dual velocity command input sensitivity, etc.) are accessible on the personality board.

Within the amplifier module, the motor velocity command and tachomoeter feedback(T) are summed and amplified to become the current reference, see FIG. 7 of the drawings.

The inner current loop then delivers the current error signal by summing the current reference with the current feeback. The polarity and amplitude of the current error signal is representative of the current delivered to the motor in question.

By utilization of the APM and CLX System, the three axis control can be achieved with the proper positioning and clamping of the pipe(P) in the testing position, engagement and operation of the milling head 40 to mill a section of the pipe(P) so that the hardness testing head 59 can be positioned in the same space to achieve an accurate test of the pipe by the engagement of the testing load cell 72 via the plunger shaft 73 and diamond penetrator 74 onto the pipe(P). The clamping load cell 76 determines proper positioning of the test head assembly and a pre-determined clamp load factor on the pipe so that accurate hardness testing can be done.

Referring to FIG. 6 of the drawings, a block flow diagram is shown of the dual clamping load cell configuration. Output from the load cells are directed through strain gauge conditioners to the microprocessor which process the data information from a variety of other sources and outputs to the servo drive controller (CLX) which in turn drives the servomotors for position control as hereinbefore described.

Figure 5:
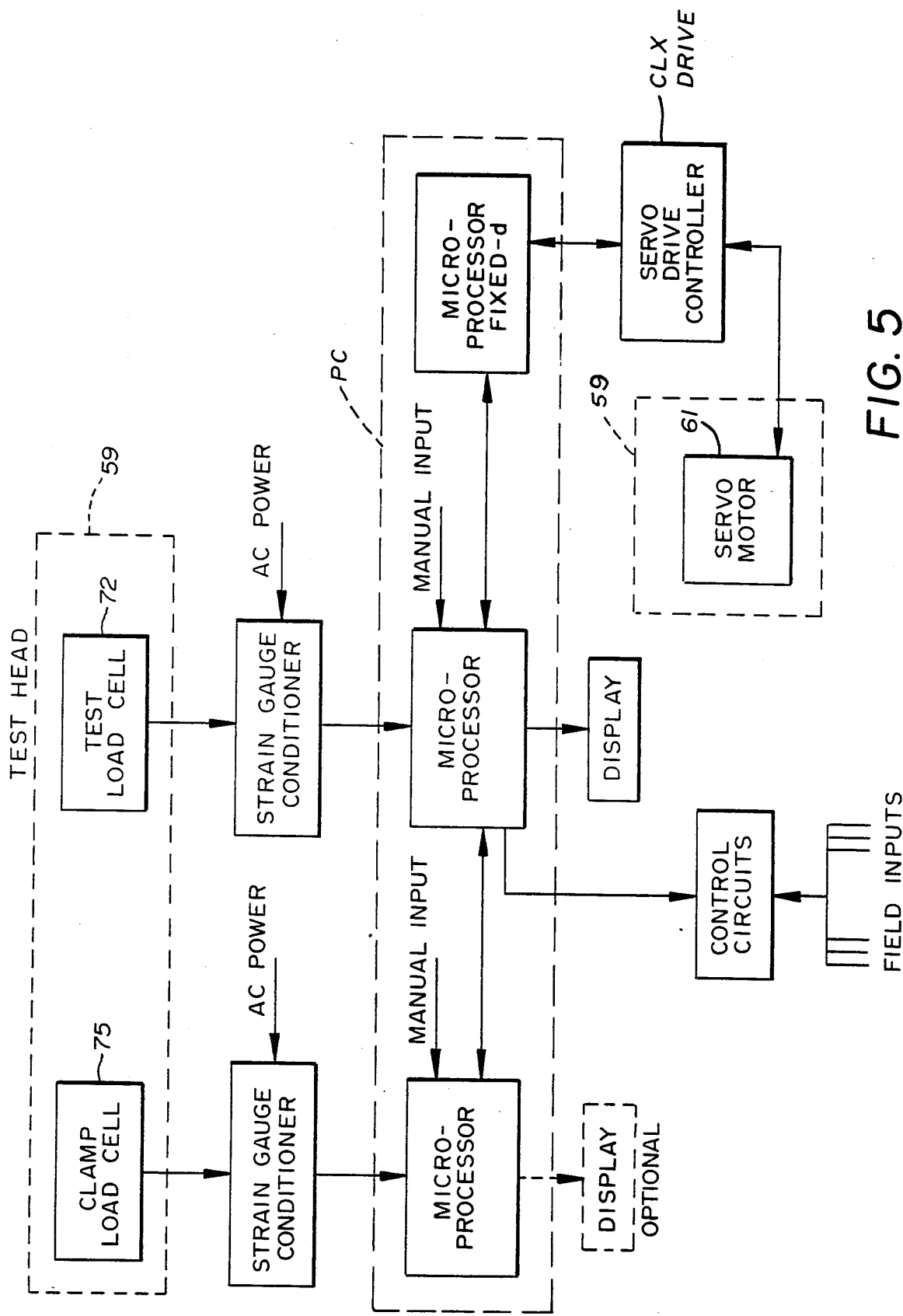
FIG. 5 is a block flow diagram of the testing head electronic control.

The PC is indicated in the drawings of FIGS. 5 and 6 as the micro-processor block which connects to all positioning and activation functions.

The testing device of this invention combines a unique clamping and testing load cell head configuration with a compact fully programmable positioning and activation control system that is fully adjustable to various pipe size and construction characteristics while maintaining a rapid, multi-step test sequence procedure insuring accurate, reliable test results within a continuous or batch material testing configuration environment.

Thus having illustrated and described our invention, what we claim is:

1. A hardness testing device comprises in combination a testing and milling head assembly, means for positioning said testing and milling head assembly in position above a work piece, means for engaging, positioning and supporting a work piece, said testing and milling head assembly comprising a milling head having a drive means, a testing head positioned adjacent said milling head, load cells with in said testing head and means for control of said testing head position, duration, and relative spacing of both the milling head and testing head with said work piece, communication means in said testing head to said control means, clamping load cells on said testing head in communication with said control means of position.

2. The hardness testing device of claim 1 wherein said means for positioning said testing and milling head assembly comprises a support frame configuration having miltiple guide tracks and support work structures and clamping load cell means.

3. The hardness testing device of claim 1 wherein said means for engaging, positioning and supporting a work piece comprises a work piece fixture secured to a movable support stand.

4. The hardness testing device of claim 1 wherein said drive means for said milling head is a drive motor.

5. The hardness testing device of claim 1 wherein said means for controlling said positioning duration and relative spacing of both the milling head and testing head comprises an integrated multiple control system having a programmable controller, an axis positioning module and a servomotor drive system, means for programming said controller and a power source.

6. The hardness testing device of claim 5 wherein said programable controller receives and assimulates a variety of data input via feed back position comparison techniques, processing the same and comparing relative position of controlled axis parameters of head assemblies to pre-programmed positions and activation of said access position and servomotor drive system to achieve program objective in test sequence.

7. The hardness testing device of claim 1 wherein said testing head assembly comprises an internal load cell stabilizer positioning mechanism for advancing the load cell into registration with said work piece.

8. The method of testing a work piece for material hardness comprising the steps of positioning the work piece to be tested, advancing a milling head to engage and clean a portion of the work piece, positioning a hardness tester head for engagement with the work piece, said hardness tester head comprising a clamping and testing load cell configuration on the work piece, computing relative values of hardness to a pre-determined standard and controlling said steps by a pre-programable controller and servodrive mechanism.

* * * * *